US008975586B2

(12) United States Patent
Krolak et al.

(10) Patent No.: US 8,975,586 B2
(45) Date of Patent: Mar. 10, 2015

(54) DIFFUSING MEASUREMENT WINDOW FOR NEAR AND MID IR MULTICHANNEL SENSOR

(75) Inventors: Adam Krolak, North Vancouver (CA); Sebastien Tixier, North Vancouver (CA)

(73) Assignee: Honeywell ASCa Inc., Mississauga (CA)

(*) Notice: Subject to any disclaimer, the term of this patent is extended or adjusted under 35 U.S.C. 154(b) by 347 days.

(21) Appl. No.: 13/153,783

(22) Filed: Jun. 6, 2011

(65) Prior Publication Data

US 2012/0305775 A1    Dec. 6, 2012

(51) Int. Cl.
```
G01J 5/02        (2006.01)
G01J 5/08        (2006.01)
G02B 5/02        (2006.01)
G01B 11/06       (2006.01)
G01N 21/3563     (2014.01)
G01N 21/84       (2006.01)
G01N 21/86       (2006.01)
G01N 21/3559     (2014.01)
```
(Continued)

(52) U.S. Cl.
CPC .............. *G01J 5/0878* (2013.01); *G02B 5/021* (2013.01); *G01J 5/0809* (2013.01); *G01B 11/06* (2013.01); *G01N 21/3563* (2013.01); *G01N 21/8422* (2013.01); *G01N 21/86* (2013.01); *G01N 2021/8427* (2013.01); *G01N 2021/8609* (2013.01); *G01N 2021/8663* (2013.01); *G01N 2201/0634* (2013.01); *G01N 21/3559* (2013.01); *G01B 11/0625* (2013.01); *G02B 5/0284* (2013.01); *G01N 21/031* (2013.01); *G01N 21/474* (2013.01); *G01N 2021/4773* (2013.01); *G01N 2021/8917* (2013.01)

USPC ...................................... 250/353; 250/339.11

(58) Field of Classification Search
USPC .............................................. 250/339.11, 353
See application file for complete search history.

(56) References Cited

U.S. PATENT DOCUMENTS 3,793,524 A * 2/1974 Howarth .................... 250/339.1
3,973,122 A * 8/1976 Goldberg ................... 250/338.1
(Continued)

FOREIGN PATENT DOCUMENTS

| EP | 2656024 A1 | 10/2013 |
|---|---|---|
| WO | 2012083428 A1 | 6/2012 |

OTHER PUBLICATIONS

Bulk scattering properties of synthetic fused silica at 193 nm, Oct. 30, 2006 / vol. 14, No. 22 / Optics Express, p. 10537-10549 to Schroder et al.*

(Continued)

*Primary Examiner* — David J Makiya
*Assistant Examiner* — Kenneth J Malkowski
(74) *Attorney, Agent, or Firm* — Cascio Schmoyer & Zervas

(57) ABSTRACT

A diffuse reflector of radiation in the near and mid infrared regions includes (i) an assembly that has a reflecting element and a diffusing element that is made of one or more layers of calcium fluoride, sapphire, or alumina; or (ii) a diffusively reflective surface configured as a metallic layer with a rough surface. The diffuse reflector can be incorporated into systems for measuring properties of sheet materials and particularly into optical sensors that include a measurement window configured with one or more of the diffuse reflectors that cause incident radiation from a sensor light source to be diffused and reflected a plurality of times within a layer of material before being detected by the sensor receiver.

23 Claims, 4 Drawing Sheets

(51) Int. Cl.
  *G01N 21/47* (2006.01)
  *G01N 21/03* (2006.01)
  *G01N 21/89* (2006.01)

(56) References Cited

U.S. PATENT DOCUMENTS

| | | |
|---|---|---|
| 4,311,658 A | 1/1982 | Nicoll |
| 4,403,010 A | 9/1983 | Festag |
| 4,582,431 A | 4/1986 | Cole |
| 4,797,246 A | 1/1989 | Reinke |
| 4,957,770 A | 9/1990 | Howarth |
| 5,230,923 A | 7/1993 | Hirokawa |
| 5,276,327 A | 1/1994 | Bossen |
| 5,543,961 A | 8/1996 | Smith |
| 5,639,671 A | 6/1997 | Bogart |
| 5,795,394 A | 8/1998 | Belotserkovsky |
| 6,018,419 A | 1/2000 | Cobb, Jr. |
| 6,074,483 A | 6/2000 | Belotserkovsky |
| 6,179,918 B1 | 1/2001 | Belotserkovsky |
| 6,183,561 B1 | 2/2001 | Belotserkovsky |
| 6,565,343 B1 | 5/2003 | Krycki |
| 6,793,854 B1 | 9/2004 | Kirjavainen |
| 6,805,899 B2 | 10/2004 | MacHattie |
| 6,836,325 B2 * | 12/2004 | Maczura et al. ............... 356/328 |
| 6,848,795 B2 | 2/2005 | Kaminsky |
| 7,223,977 B2 | 5/2007 | Shelly |
| 7,291,856 B2 | 11/2007 | Haran |
| 7,321,425 B2 | 1/2008 | Haran |
| 7,382,456 B2 * | 6/2008 | Tixier et al. .................... 356/419 |
| 7,436,469 B2 | 10/2008 | Gehlsen |
| 7,452,356 B2 | 11/2008 | Grove |
| 7,763,876 B2 | 7/2010 | Banton |
| 7,868,287 B2 | 1/2011 | Fry |
| 2003/0057053 A1 * | 3/2003 | Kano et al. ............... 194/207 |
| 2003/0129404 A1 | 7/2003 | Argoitia |
| 2004/0169857 A1 | 9/2004 | Acosta |
| 2007/0153281 A1 * | 7/2007 | Gordon et al. ................. 356/419 |
| 2010/0014164 A1 | 1/2010 | O'Brien |

OTHER PUBLICATIONS

PCT International Search Report for PCT/CA2012/000542 dated Aug. 31, 2012.

* cited by examiner

DIFFUSING MEASUREMENT WINDOW FOR NEAR AND MID IR MULTICHANNEL SENSOR

FIELD OF THE INVENTION

The present invention generally relates to a diffuse reflector for radiation in the near and mid infrared regions. The diffuse reflector can be incorporated into systems for measuring properties of sheet materials and particularly into optical sensors that include a measurement window configured with one or more of the diffuse reflectors that cause incident radiation from a sensor light source to be diffused and reflected a plurality of times within a layer of material before being detected by the sensor receiver.

BACKGROUND OF THE INVENTION

In the manufacture of sheet materials, it is well known that various sheet properties can be detected "on-line," that is, while a sheet making machine is operating. On-line measurement devices measure sheet properties such as thickness, basis weight, moisture content, chemical composition and the like. Typically, such on-line devices employ sensors that periodically traverse, or scan, the moving sheets in the cross direction, which is perpendicular to the machine direction of sheet travel.

U.S. Pat. No. 3,793,524 to Howarth describes an infrared sensor to determine the amount of moisture in a sheet of material such as paper that has radiation diffusing and absorbing properties. The IR sensor has a radiation source and a detector, which is offset from the source. The detector measures radiation that has impinged upon the sheet of material and includes a pair of opposing planar paper guides that define a path for the moving sheet. Each paper guide has a reflective anodized aluminum reflective coating with a layer of translucent quartz or glass ceramic, which acts as diffuser. In operation, the configuration of the paper guides causes the radiation to follow multiple simultaneous random paths crossing through the paper to enhance the sensitivity of the sensor. Current IR sensors employ paper guides that are constructed of layers of TELFON and quartz that are secured to a reflective surface. Unfortunately, IR sensors incorporating this design are not accurate over a significant portion of the mid IR range

SUMMARY OF THE INVENTION

Prior art paper guides or plates have a significant absorption at wavelengths greater than approximately 2.7 microns that makes measurement of materials with infrared signatures above 2.7 microns difficult or impossible. The present invention is based in part of the development of a diffuse reflector that is transparent and exhibits Lambertian reflectance of near and mid-IR energy up to 5 microns or more.

In one aspect, the invention is directed to a diffuse reflector over the near and mid-infrared range that includes:

(i) a diffuser assembly comprising a reflecting element and diffusing element that comprises one or more layers that is formed of calcium fluoride, sapphire, or alumina; or (ii) a diffusively reflective surface comprising a metallic layer with a rough surface. The diffuser assembly or diffusively reflective surface, along with the light source, functions as a diffuse source of illumination. When the diffuse reflector employs a metallic layer, the metallic surface will function as both a reflective and diffusive surface and therefore the metal layer does not require an underlying reflective surface. The diffusely reflective metallic surface is created, for example, by coating a metal layer on a rough surface or by subjecting a smooth metallic layer to surface treatment.

In another aspect, the invention is directed to an apparatus for sensing a layer of material that includes:

a radiation source, disposed on one side of the layer of material, that directs a beam of incident radiation into the layer of material;

a radiation receiver that detects at least a portion of a reflected beam that propagates through the layer of material; and one or more members that define a measurement cell with a path for the layer of material, wherein each member includes a diffuser, facing a side of the layer of material, and comprises of (i) at least one layer of material, that comprises calcium fluoride, sapphire and/or alumina that is formed on a specular reflective surface or (ii) a diffusively reflective surface comprising metallic layer with a rough surface, wherein the measurement cell is configured to cause radiation to be reflected through the layer of material a plurality of times before being detected by the radiation receiver.

In yet another aspect, the invention is directed to an infrared sensor, for measuring physical characteristics of a sheet product moving in the machine direction, that includes:

a housing supporting a radiation source and a radiation receiver, wherein the radiation source directs a beam of incident infrared radiation into the sheet product; and reflective means disposed between the radiation source and the radiation receiver for reflecting radiation toward the sheet product such that radiation is reflected through the sheet product a plurality of times before reaching the radiation detector and the radiation propagates through the sheet product in the machine direction, wherein the reflective means includes a diffuser material comprising (i) calcium fluoride, sapphire or alumina or (ii) a metallic layer with a roughened surface.

The diffuse reflector is particularly suited for used in multichannel sensors. The Lambertian-type light scattering generated by the diffusing element affords many benefits. Because the light interacts multiple times with the layer(s) of material, the sensor's sensitivity to selected Components within the layer is enhanced. The diffuse deflector of the present invention does not require quartz or TEFLON layers.

DETAILED DESCRIPTION OF PREFERRED EMBODIMENTS

Figure 1:
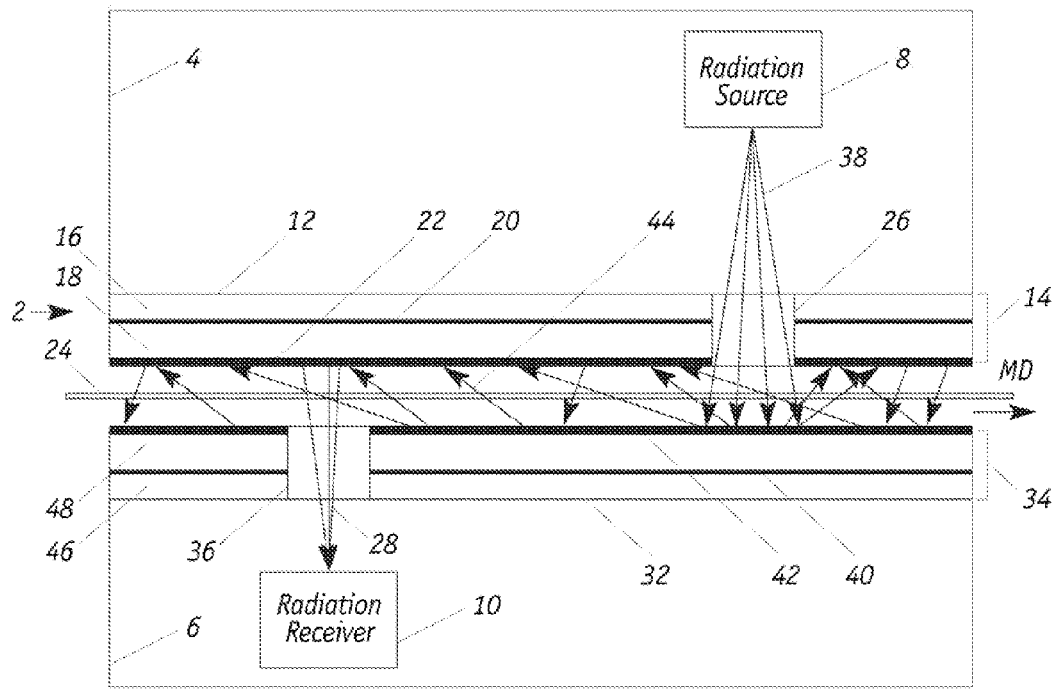
FIGS. 1, 2, 3 and 4 depict infrared sensors incorporating diffuse reflector assemblies of the present invention.

FIG. 1 illustrates a non-contacting optical sensor 2 that includes enclosures 4 and 6 (each also called "scanner head" or "head") that house sensor components for measuring qualities, characteristics or features of a moving web 24 that can be monitored which include, but are not limited, to single and multi-layered compositions, coatings, films, webs or sheets. While the sensor will be illustrated in measuring characteristics in paper and plastic, it is understood that the sensor can be employed to detect a variety of components in a number of different materials including, for example, coated materials, fabrics, and the like. Sensor 2 is particularly suited for measuring the thickness or weight of a layer of light transmissive material 24 moving in the machine direction (MD). Scanner 2 includes a radiation or light source 8 that is positioned in head 4 and a radiation receiver or detector 10 that is positioned in head 6. An upper diffuse reflector plate assembly 14, which is secured to operative surface 12 of head 4, comprises a reflective element 16, such as a specular mirror, that is covered with a layer or plate 18 of calcium fluoride ($CaF_2$) or sapphire. One embodiment of the specular mirror consists of an aluminum coating that is formed on a polyimide (KAPTON) film. Outer surface 22 of layer 18 is preferably polished to make it easier to clean and to render it more resistant to moisture whereas inner surface 20 is highly roughened to serve as a diffusive surface. Similarly, a lower diffuse reflector plate assembly 34, which is secured to operative surface 32 of head 6, comprises a reflective element 46, such as a specular mirror, that is covered with a layer or plate 48 of calcium fluoride or sapphire. Outer surface 42 of layer 48 can also be polished whereas inner surface 40 is highly roughened to serve as a diffusive surface.

The upper and lower scanner heads 4, 6 are aligned so that planar polished surface 22 of upper scanner head 4 is parallel with and faces planar polished surface 42 of the lower scanner head 6. Apertures 26 and 36 provide access to light source 8 and receiver 10, respectively, and they can be covered with a window material such as calcium fluoride or sapphire, which affords mechanical strength and seals the plates from moisture. Apertures 26 and 36, which are configured on opposite sides of moving web 24, are not aligned, that is, as shown, light source 8 and receiver 10 define respective axes of radiation that are laterally offset from one another along the MD path of moving web 24. In this fashion, the arrangement of upper and lower diffuse reflector plates 14, 34 define a measurement window or cell through which web material 24 travels. In operation of sensor 2, a lens in light source 8 focuses incident radiation 38 through aperture 26 toward moving web 24 and a lens is positioned to collect radiation 28 that is reflected from polished surface 22 through aperture 36. Movement of the upper and lower scanner heads 4, 6 in the cross direction, which is traverse to the MD, is coordinated so that light is diffused and reflected by plate assemblies 14, 34 as radiation 44 propagates through layer of material 24 multiple times before being detected by receiver 10.

Light diffusing elements that scatter or diffuse light generally function in one of three ways: (a) as a surface light diffusing element utilizing surface roughness to scatter light in a number of directions, (b) as a bulk light diffusing element with flat outer surfaces and embedded light-scattering elements, or (c) as a combination of elements (a) and (b). The bulk diffuser diffuses the light within the material. Diffusion is achieved by light scattering as it passes through materials with varying indexes of refraction. The term "diffuser" or "diffuser member" means any material that is able to diffuse specular light (light with a primary direction) to a diffuse light (light with random direction). The term "light" means electromagnetic radiation having wavelength in ranges that are suited for measuring properties of a layer material with sensors of the present invention. Near infrared and/or mid-infrared radiation is particularly suited for measuring physical characteristics of paper and plastic products.

Calcium fluoride and sapphire are transparent to near and mid-infrared radiation. The randomly roughened surfaces 20, 40 can be produced by electric discharge techniques, mechanical grinding, or etching to create a plurality of randomly oriented and spaced facets and cavities for diffusively reflecting incident near and mid infrared radiation.

Light source 8 can comprise, for instance, a Quartz Tungsten Halogen lamp to irradiate material 24 with radiation having wavelengths in at least first and second separate wavelength regions of the electromagnetic spectrum that are referred to as reference and measurement wavelength bands as further described herein.

In the arrangement of radiation source 8, radiation receiver 10 shown in FIG. 1, reflected light 44 travels in a direction that is parallel to the MD so that the cross direction (CD) resolution of sensor 2 is maintained. Although reflected radiation 44 shown in FIG. 1 is depicted as traveling "downstream" in the opposite machine direction as web 24, this feature is not critical to the sensor's function. In other words, sensor 2 will operate even if web 24 moves in the opposite direction so that the reflected radiation is moving "upstream" relative to the web; the critical feature is that incident radiation 38 that emitted from light source 8 travel along a path that is parallel to that of moving web 24 as reflected radiation 44 moves toward receiver 10.

Figure 2:
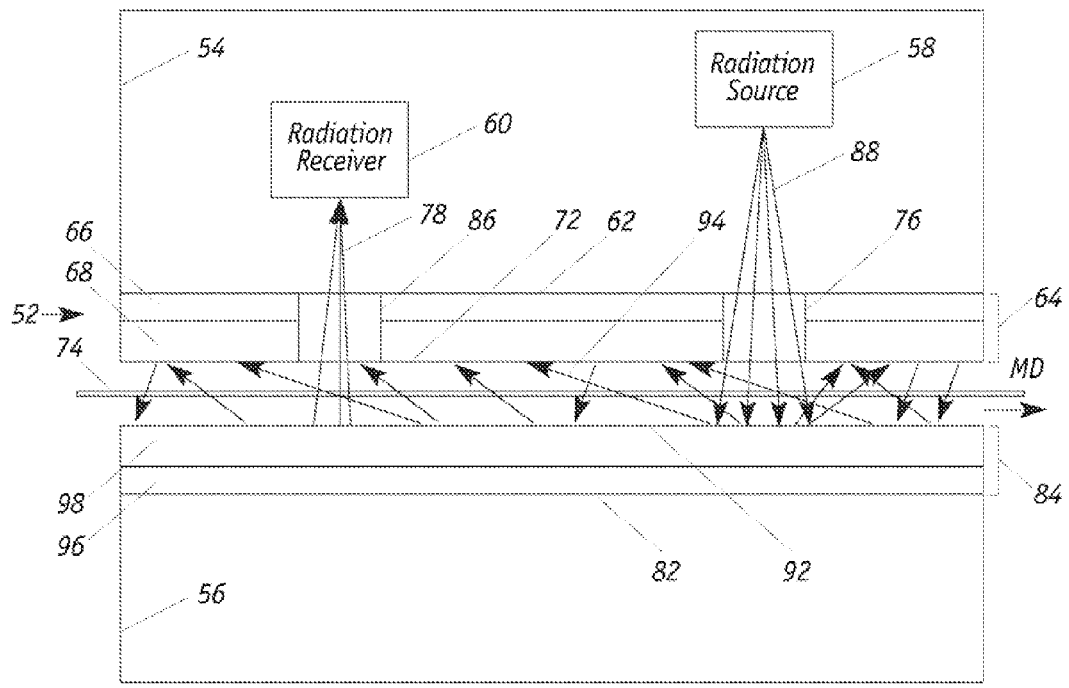

FIG. 2 illustrates a non-contacting optical sensor 52, which includes scanner head 54 that houses light source 58 and receiver or detector 60, for measuring physical qualities, characteristics or features of a layer of light transmissive material 74 moving in the MD. An upper diffuse reflector plate assembly 64, which is secured to operative surface 62 of head 54, comprises a reflective element 66, such as a specular mirror, that is covered with a layer or plate 68 made of alumina ($Al_2O_3$). Similarly, a lower diffuse reflector plate assembly 84, which is secured to operative surface 82 of head 56, comprises a reflective element 96, such as a specular mirror, that is covered with a layer or plate 98 of alumina.

The upper and lower scanner heads 54, 56 are aligned so that planar surface 72 of alumna plate 68 is parallel with and faces planar surface 92 of alumina plate 98. Apertures 76 and 86 provide access to light source 58 and receiver 60, respectively, and they can be equipped with a window material, which can be roughened on one side or not, such as calcium fluoride or sapphire. The upper and lower diffuse reflector plates 64, 84 form a measurement window or cell through which web material 74 travels. In operation of single-side sensor 52, a lens in light source 58 focuses incident radiation 88 through aperture 76 toward moving web 74 and a lens is positioned to collect radiation 78 that is reflected from surface 92 through aperture 86. Movement of the upper and lower scanner heads 54, 56 in the cross direction is coordinated so that light is diffused and reflected between plate assembles 64, 84 as radiation 94 propagates through layer of material 74 multiple times before being detected by receiver 60. Alumina, which is translucent to near and mid infrared radiation, serves as a bulk light-diffusing element. The alumina layer is typically smooth on both sides.

Figure 3:
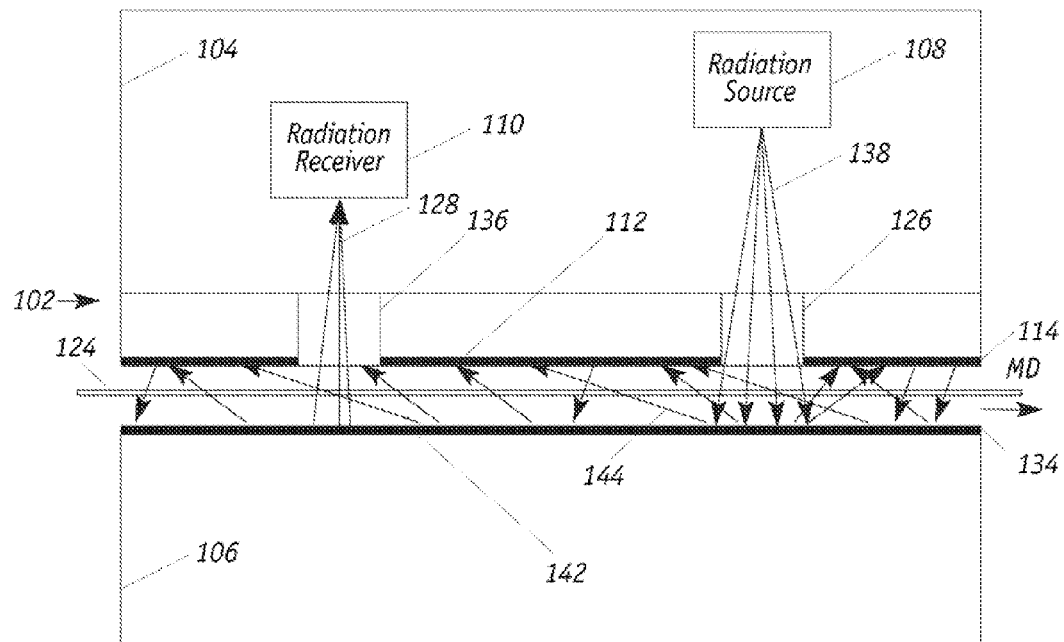

FIG. 3 illustrates another single-sided non-contacting optical sensor 102, which includes scanner head 104 that houses light source 108 and receiver or detector 110, for measuring physical qualities, characteristics, or features of a layer of light transmissive material 124 moving in the MD. An upper diffuse reflector plate assembly 114, which is formed on operative surface 112 of head 104, comprises a reflective element consisting of a roughened operative surface that is coated with a metallic reflective coating. Alternatively, the reflective element consists of a diffusively reflective metallic surface. Similarly, a lower diffuse reflector plate assembly 134 has an operative surface 142 on head 106 that has a reflective element of the same construction. Suitable metallic coatings can be formed, for example, from gold, silver, and aluminum by electrochemical plating.

The upper and lower scanner heads 104, 106 are aligned so that surface 112 of upper scanner head 104 is parallel with and faces surface 142 of lower scanner head 106. Apertures 126 and 136 provide access to light source 108 and receiver 110, respectively; the apertures can be optionally equipped with a calcium fluoride or sapphire window, which is roughened on one side or not. The upper and lower diffuse reflector plates 114, 134 define a measurement window or cell through which web material 124 travels. In operation of single-side sensor 102, a lens in light source 108 focuses incident radiation 138 through aperture 126 toward moving web 124 and a lens is positioned to collect radiation 128 that is reflected from surface 142 through aperture 136. Movement of the upper and lower scanner heads 104, 106 in the cross direction is coordinated so that light is diffused and reflected between plate assemblies 114 and 134 as radiation 144 propagates through layer of material 124 multiple times before being detected by receiver 110. In this sensor 102, the roughened metallic coating (or the diffusively reflective metallic surface) functions both as diffuser and reflective elements.

Figure 4:
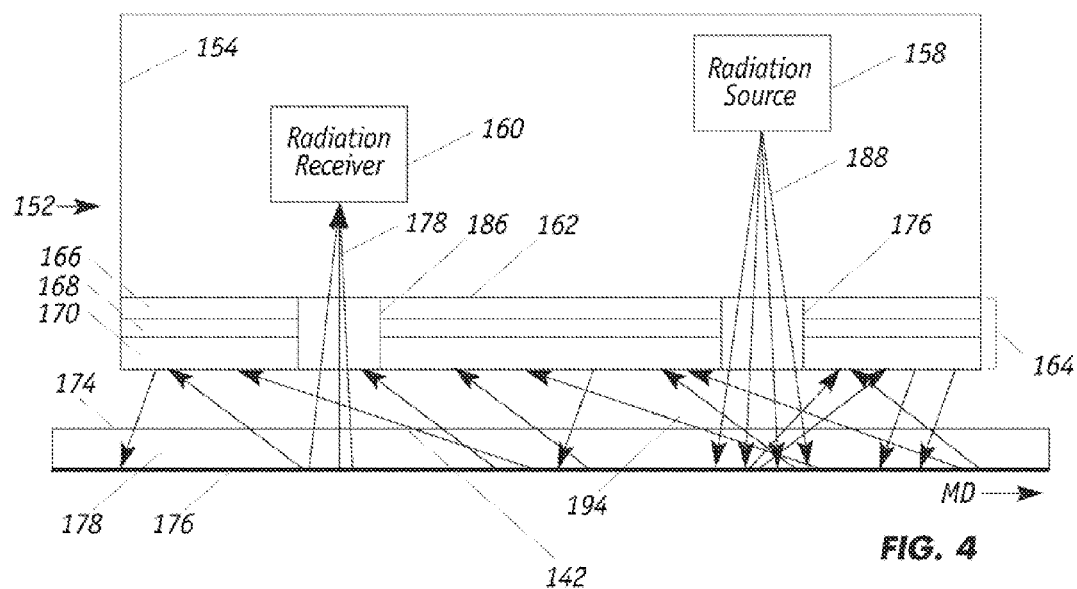

FIG. 4 illustrates a non-contacting optical sensor 152 that is particularly suited for measuring properties such as the thickness or weight, for example, of a web 174 comprising a layer of material 178 that is coated on a reflective laminant substrate 176. The sensor 152 includes head 154 that houses radiation source 158 and radiation receiver 160. An upper diffuse reflector plate assembly 164, which is secured to operative surface 162 of head 154, comprises a reflective element 166, such as a specular mirror, that is covered with a layer of alumina 168 and a layer or plate of calcium fluoride or sapphire 170, which is polished. In this construction, the alumina serves as the diffusing material.

A lens within radiation source 158 focuses incident radiation 188 through aperture 176 toward moving web 174 and a lens is positioned to collect radiation 178 that is reflected from reflective laminant substrate 176 of moving web 174 through aperture 186. With this configuration of the single-sided sensor, incident light 194 from light source 158 is diffused and reflected by reflective laminant substrate 176 and plate assembly 164 multiple times before receiver 160 detects the light. As shown in FIG. 4, the non-contacting optical sensor 152 measures properties of one or more layers of material 174 that are coated on reflective laminant substrate 176. It is also apparent that the same sensor 152 can operate to measure layer of material 178 prior to being coated onto the reflective laminant substrate 176. In other words, so long as reflective laminant substrate 176 is underneath layer of material 178 to reflect radiation, sensor 152 will operate.

The single-sided infrared sensor of FIG. 4 can also be configured to analyze a layer of material that is not formed on a reflective laminant substrate. This is readily achieved by employing an external reflective member that is positioned adjacent the lower surface of the layer of material.

Figure 5:
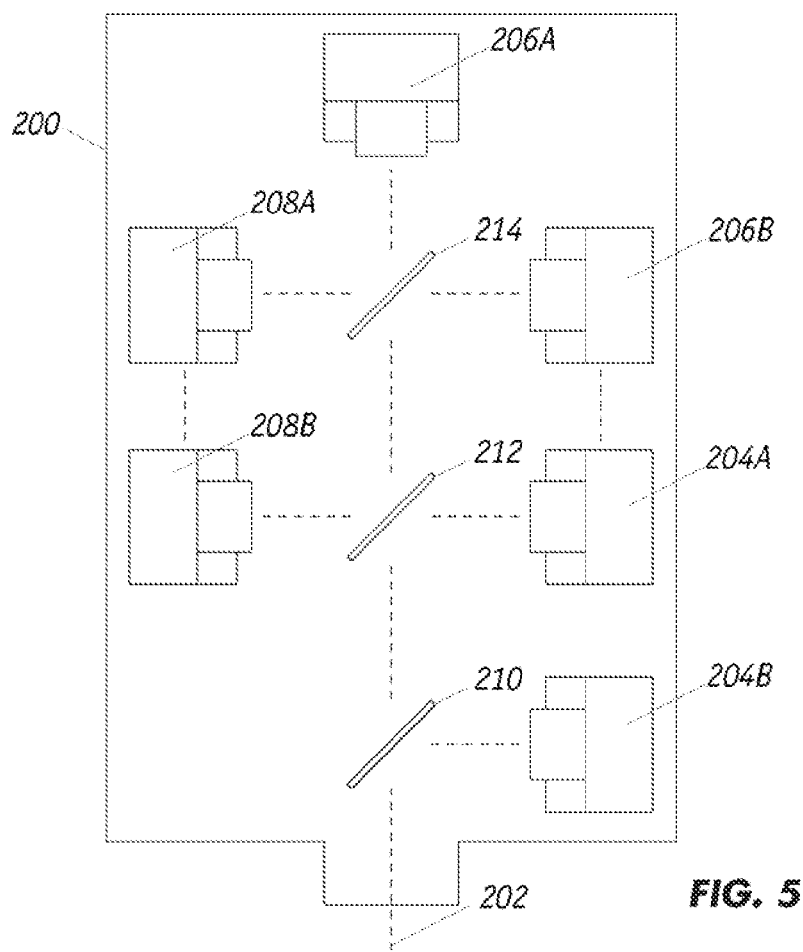
FIGS. 5 and 6 illustrate the light receivers.
Figure 6:
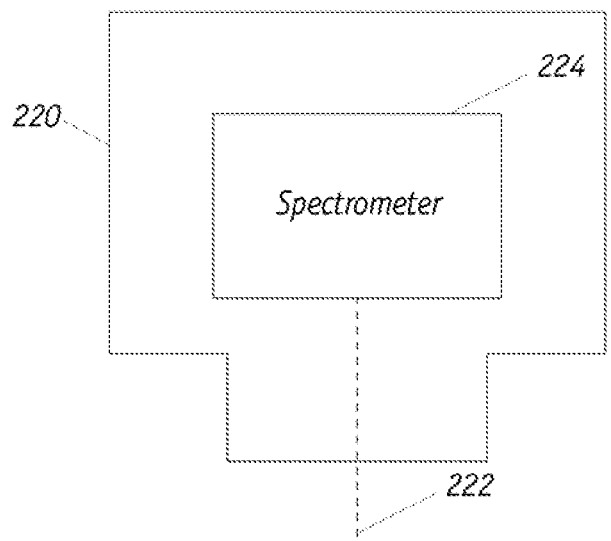

FIG. 5 illustrates a suitable receiver that includes a detector assembly 200 that houses a six-channel sensor for measuring three properties in a layer of material. In this arrangement, there are three measurement filter/detectors 204A, 206A and 208A and three corresponding reference filter/detectors 204B, 206B, and 208B. A separate infrared band pass filter is positioned before each detector; in this fashion, each of the infrared detectors measures the intensity of only the portion of the infrared beam spectrum that falls within the band pass of the associated filter. A broadband infrared source of energy (not shown) directs incident radiation onto the layer of material to be analyzed and reflected radiation 202 is wavelength-analyzed by passing the beam through beam splitters 210, 212, 214 and the appropriate filters to the individual detectors. As is apparent, additional pairs of measure and reference detector/filters can be incorporated as needed. Suitable light sources and associated detector arrangements are described, for instance, in U.S. Pat. No. 4,957,770 to Howarth, U.S. Pat. No. 7,291,856 to Haran et al., and U.S. Pat. No. 7,382,456 to Tixier et al., which are incorporated herein by reference. Alternatively, as shown in FIG. 6, the receiver comprises a detector assembly 220 that employs a spectrometer 224 that analyzes reflected radiation 222.

Figure 7:
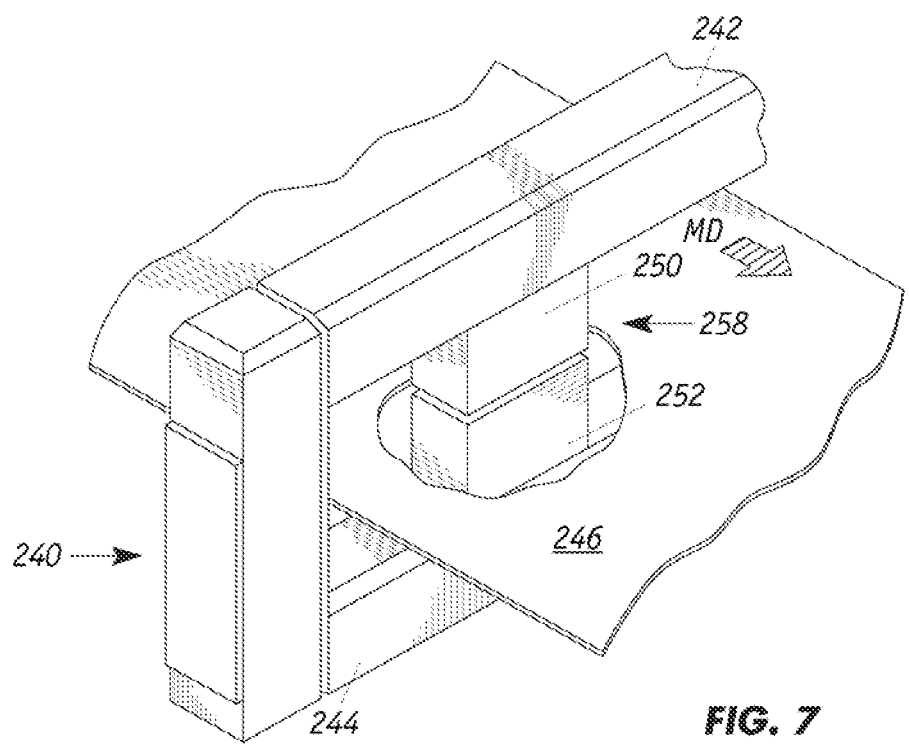
FIG. 7 shows a sheetmaking system implementing the sensor in a dual scanner.

FIG. 7 illustrates one particular implementation of the sensor that is shown in FIGS. 1, 2 and 3. In particular, the radiation source and detector are housed in a dual head scanner 258 of scanner system 240 which can be employed to measure the moisture content in paper or the concentration of polymer films. Upper scanner head 250 moves repeatedly back and forth in the CD across the width of the moving sheet 246, which moves in the MD, so that the characteristics of the entire sheet may be measured. Scanner 258 is supported by two transverse beams 242, 244 on which are mounted upper and lower scanning heads 250, 252. The operative faces of the lower and upper scanner heads 250, 252 define a measurement window or cell that accommodates sheet 246. The lower scanner head 252 may include a sheet stabilization system such as an air-bearing stabilizer (not shown) to maintain the sheet on a consistent plane as it passes through the measurement cell. The movement of the dual scanner heads 250, 252, is synchronized with respect to speed and direction so that they are aligned with each other.

One technique of monitoring the thickness of a plastic film measures the concentration(s) (weights per unit area, typically measured in grams per square meter, gsm) of the particular polymer(s) that form the film. Multilayer films typically comprise a plurality of layers that are laminated together. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The sensor of the present invention, among other things, is effective in controlling the production of multilayer films to assure that each layer in the film has the proper thickness or weight (gsm) so that the multilayer film has the right combination of properties.

If the density of a particular polymer component in the multilayer film is known the thickness of the film component can be determined. The thickness can be calculated with a computer. Commonly the film thickness is not calculated and the weight (gsm) of the component is all that is required by the user for quality control.

The foregoing has described the principles, preferred embodiments and modes of operation of the present invention. However, the invention should not be construed as being limited to the particular embodiments discussed. Thus, the above-described embodiments should be considered as illustrative rather than restrictive, and it should be appreciated that variations may be made in those embodiments by workers skilled in the art without departing from the scope of the present invention as defined by the following claims.

What is claimed is:

1. An apparatus for sensing a layer of material that comprises:
   a radiation source, disposed on one side of the layer of material, that directs a beam of incident near and mid infrared radiation having wavelengths of more than 5 microns into the layer of material;
   a radiation receiver that detects at least a portion of a reflected beam that propagates through the layer of material; and one or more members that define a measurement cell with a path for the layer of material, wherein each member includes a diffuser comprising a layer of alumina, which is translucent to the near and mid infrared radiation from the radiation source, and that is formed on a specular reflective surface, wherein the layer of alumina has a smooth side that faces and is adjacent to a side of the layer of material and wherein the measurement cell is configured to cause radiation to be reflected through the layer of material a plurality of times before being detected by the radiation receiver and wherein the diffuser does not include quartz or plastic.

2. The apparatus of claim 1 comprising a pair of members that defines a measurement cell for the layer of material, wherein the radiation source and radiation receiver have respective axes of radiation and detection that are laterally offset from one another with respect to the path.

3. The apparatus of claim 1 comprising a single member and wherein the layer of material is formed on a sheet of reflective substrate that is positioned facing the single member and wherein the single member and reflective substrate define the measurement cell and path for the layer of material.

4. The apparatus of claim 1 wherein for each member the layer of alumina has a first side with a smooth surface which faces and is adjacent to the layer of material and a second side with a smooth surface which covers the specular reflective surface.

5. The apparatus of claim 2 wherein the pair of members includes a first member that has a first plate and a second member that has a second plate, wherein the first and second plates are substantially parallel and the plates are positioned on opposite sides and substantially parallel to the layer of material, wherein the first plate has a first aperture that is coupled to the radiation source and wherein the second plate has a second aperture that is coupled to the radiation receiver.

6. The apparatus of claim 1 wherein the pair of members includes a first member that has a first plate and a second member that has a second plate, wherein the first plate and second plate are substantially parallel and the plates are positioned on opposite sides and substantially parallel to the layer of material, wherein the first plate has a first aperture that is coupled to the radiation source and wherein the first plate has a second aperture that is coupled to the radiation receiver.

7. The apparatus of claim 1 wherein the reflective surface comprises a mirror.

8. The apparatus of claim 1 wherein the radiation source includes a sapphire window through which the radiation exits and the radiation receiver includes a sapphire window through which radiation enters.

9. An infrared sensor, for measuring physical characteristics of a sheet product moving in the machine direction, that comprises:
a housing supporting a radiation source and a radiation receiver, wherein the radiation source directs a beam of incident infrared radiation having wavelengths of more than 5 microns into the sheet product; and
reflective means disposed between the radiation source and the radiation receiver for reflecting radiation toward the sheet product such that radiation is reflected through the sheet product a plurality of times before reaching the radiation receiver and the radiation propagates through the sheet product in the machine direction, wherein the reflective means includes a diffuser material comprising a layer of alumina which is translucent to the incident infrared radiation, wherein the layer of alumina has a smooth surface that faces and is adjacent to the sheet product and wherein the diffuser material does not include quartz or plastic.

10. The infrared sensor of claim 9 wherein the housing comprises a first scanner head and a second scanner head and wherein the first and second scanner heads move in a synchronized fashion along a cross direction and define a path for the sheet product, wherein the first scanner head comprises a first diffuser assembly comprising a first reflecting element and a first diffusing element, which faces and is adjacent to the first side of the sheet product, wherein the first diffusing element comprises a layer of alumina which is translucent to the incident infrared radiation, and wherein the second scanner head comprises a second diffuser assembly comprising a second reflecting element and a second diffusing element, which faces and is adjacent to the second side of the sheet product, wherein the second diffusing element comprises a layer of alumina which is translucent to the incident infrared radiation.

11. The infrared sensor of claim 10 wherein the first reflective element is formed on a plate that has a first aperture or sapphire window that is coupled to the radiation source and wherein the second reflective element is formed on a second plate that has a second aperture or sapphire window that is coupled to the radiation detector.

12. The infrared sensor of claim 10 wherein the first scanner head comprises the first diffuser assembly that includes a first specular reflecting surface on a side adjacent the first side of the sheet product and a first layer of alumina that is disposed on the first specular reflecting surface and wherein the second scanner head comprises the second diffuser assembly that includes a second specular reflecting surface on a side adjacent the second side of the sheet product and a second layer of alumina that is disposed on the second specular surface.

13. The infrared sensor of claim 10 wherein the first diffusing element has a first polished surface and the second diffusing element has a second polished surface.

14. The infrared sensor of claim 9 wherein the layer of alumina has a first side with a smooth surface that faces and is adjacent to the sheet product and a second side with a smooth surface that covers a specular reflective surface.

15. An apparatus for sensing a layer of material that comprises:
a radiation source, disposed on one side of the layer of material, that directs a beam of incident near and mid infrared radiation having wavelengths of more than 5 microns into the layer of material;
a radiation receiver that detects at least a portion of a reflected beam that propagates through the layer of material; and
one or more members that define a measurement cell with a path for the layer of material, wherein each member includes a diffuser comprising at least one layer of transparent material that comprises calcium fluoride and/or sapphire that is formed on a specular reflective surface wherein the transparent material has a polished outer surface that faces and is adjacent to a side of the layer of material and a roughened inner surface and wherein the measurement cell is configured to cause radiation to be reflected through the layer of material a plurality of times before being detected by the radiation receiver and wherein the diffuser does not include quartz or plastic.

16. The apparatus of claim 15 comprising a pair of members that defines a measurement cell for the layer of material, wherein the radiation source and radiation receiver have respective axes of radiation and detection that are laterally offset from one another with respect to the path.

17. The apparatus of claim 15 comprising a single member and wherein the layer of material is formed on a sheet of reflective substrate that is positioned facing the single member and wherein the single member and reflective substrate define the measurement cell and path for the layer of material.

18. The apparatus of claim 16 wherein the pair of members includes a first member that has a first plate and a second member that has a second plate, wherein the first and second plates are substantially parallel and the plates are positioned on opposite sides and substantially parallel to the layer of material, wherein the first plate has a first aperture that is coupled to the radiation source and wherein the second plate has a second aperture that is coupled to the radiation receiver.

19. The apparatus of claim 16 wherein the pair of members includes a first member that has a first plate and a second member that has a second plate, wherein the first plate and second plate are substantially parallel and the plates are positioned on opposite sides and substantially parallel to the layer of material, wherein the first plate has a first aperture that is coupled to the radiation source and wherein the first plate has a second aperture that is coupled to the radiation receiver.

20. An infrared sensor, for measuring physical characteristics of a sheet product moving in the machine direction, that comprises:
  a housing supporting a radiation source and a radiation receiver, wherein the radiation source directs a beam of incident infrared radiation having wavelengths of more than 5 microns into the sheet product; and
  reflective means disposed between the radiation source and the radiation receiver for reflecting radiation toward the sheet product such that radiation is reflected through the sheet product a plurality of times before reaching the radiation receiver and the radiation propagates through the sheet product in the machine direction, wherein the reflective means includes a diffuser material comprising layer of transparent calcium fluoride and/or sapphire covering a reflective element, wherein the layer of transparent calcium fluoride and/or sapphire has an outer polished surface facing and adjacent to the sheet product and a roughened inner surface disposed on the reflective element, and wherein the diffuser material does not include quartz or plastic.

21. The infrared sensor of claim 20 wherein the housing comprises a first scanner head and a second scanner head and wherein the first and second scanner heads move in a synchronized fashion along a cross direction and define a path for the sheet product, wherein the first scanner head comprises a first diffuser assembly, facing the first side of the sheet product, comprising a first reflecting element and a first diffusing element, wherein the first diffusing element comprises one or more layers that is formed of calcium fluoride and/or sapphire, wherein the diffusing element has an outer polished surface facing and adjacent to the sheet product and a roughened inner surface disposed on the first reflecting element and wherein the second scanner head comprises a second diffuser assembly, facing the second side of the sheet product, comprising a second reflecting element and a second diffusing element, wherein the second diffusing element comprises one or more layers that is formed of calcium fluoride and/or sapphire wherein the second diffusing element has an outer polished surface facing and adjacent to the sheet product and a roughened inner surface disposed on the second reflecting element.

22. The infrared sensor of claim 21 wherein the first reflective element is formed on a plate that has a first aperture or sapphire window that is coupled to the radiation source and wherein the second reflective element is formed on a second plate that has a second aperture or sapphire window that is coupled to the radiation detector.

23. The infrared sensor of claim 21 wherein the first scanner head comprises the first diffuser assembly that includes a first specular reflecting surface on a side adjacent the first side of the sheet product and a first layer of calcium fluoride or sapphire that is disposed on the first specular reflecting surface and wherein the second scanner head comprises the second diffuser assembly that includes a second specular reflecting surface on a side adjacent the second side of the sheet product and a second layer of calcium fluoride or sapphire that is disposed on the second specular surface.

* * * * *